United States Patent
Lavelle

(10) Patent No.: US 9,033,956 B2
(45) Date of Patent: May 19, 2015

(54) ELECTRICALLY CHARGED MEDICAL DEVICE

(75) Inventor: Shay James Lavelle, Annacotty (IE)

(73) Assignee: Cook Medical Technologies LLC, Bloomington, IN (US)

(*) Notice: Subject to any disclaimer, the term of this patent is extended or adjusted under 35 U.S.C. 154(b) by 31 days.

(21) Appl. No.: 13/595,371

(22) Filed: Aug. 27, 2012

(65) Prior Publication Data

US 2013/0060238 A1 Mar. 7, 2013

Related U.S. Application Data

(60) Provisional application No. 61/531,178, filed on Sep. 6, 2011.

(51) Int. Cl.
*A61M 27/00* (2006.01)
*A61F 2/88* (2006.01)
*A61M 25/00* (2006.01)
*A61N 1/20* (2006.01)

(52) U.S. Cl.
CPC ............... *A61M 27/008* (2013.01); *A61F 2/88* (2013.01); *A61M 25/0017* (2013.01); *A61N 1/20* (2013.01)

(58) Field of Classification Search
CPC .......... A61M 27/008; A61M 25/0017; A61M 27/002
USPC .......................................... 604/544
See application file for complete search history.

(56) References Cited

U.S. PATENT DOCUMENTS

| | | | |
|---|---|---|---|
| 4,913,683 A | 4/1990 | Gregory | 604/8 |
| 4,930,496 A | 6/1990 | Bosley, Jr. | 128/24 |
| 4,957,479 A | 9/1990 | Roemer | 604/8 |
| 5,092,871 A | 3/1992 | Aebischer et al. | 606/152 |
| 5,441,516 A | 8/1995 | Wang et al. | 606/198 |
| 5,545,213 A * | 8/1996 | Keogh et al. | 600/36 |
| 5,554,189 A | 9/1996 | De La Torre | 623/11 |

(Continued)

FOREIGN PATENT DOCUMENTS

| | | | | |
|---|---|---|---|---|
| EP | 1 609 494 A1 | 12/2005 | | A61L 31/16 |
| GB | 2 426 199 A | 11/2006 | | A61M 25/00 |

(Continued)

OTHER PUBLICATIONS

Hildebrandt, P., et al., Prevention of surface encrustation of urological implants by coating with inhibitors, Biomaterials 22 (2001) pp. 503-507.

(Continued)

*Primary Examiner* — Philip R Wiest
*Assistant Examiner* — Ariana Zimbouski
(74) *Attorney, Agent, or Firm* — Brinks Gilson & Lione

(57) ABSTRACT

A medical device with an outer surface prepared to reduce crystalline growth or surface fowling thereon is provided. The device includes an elongate member that extends between a distal end and a proximal end, and a lumen defined through at least a central portion of the member. The member is defined from a wire that is coiled to define the lumen therethrough, the coils of the wire are configured such that a plurality of the neighboring coils define a small space therebetween. The coiled wire includes a central metallic core that extends along the entire length of the wire defining the member and a polymeric jacket is wrapped around the core, wherein the polymeric jacket is configured to retain an electric charge disposed therethrough.

10 Claims, 8 Drawing Sheets

(56) References Cited

U.S. PATENT DOCUMENTS

| | | | |
|---|---|---|---|
| 5,582,619 A | 12/1996 | Ken | 606/191 |
| 5,643,254 A | 7/1997 | Scheldrup et al. | 606/32 |
| 5,690,667 A | 11/1997 | Gia | 606/191 |
| 6,033,413 A | 3/2000 | Mikus et al. | 606/108 |
| 6,096,034 A | 8/2000 | Kupiecki et al. | 606/32 |
| 6,280,457 B1 | 8/2001 | Wallace et al. | 606/200 |
| 6,458,119 B1 | 10/2002 | Berenstein et al. | 606/1 |
| 6,555,225 B1 * | 4/2003 | Yoshioka et al. | 428/411.1 |
| 6,582,472 B2 | 6/2003 | Hart | 623/23.7 |
| 6,652,536 B2 | 11/2003 | Mathews et al. | 606/113 |
| 7,087,661 B1 | 8/2006 | Alberte et al. | 523/122 |
| 7,455,875 B2 * | 11/2008 | Weber et al. | 427/2.24 |
| 7,550,012 B2 | 6/2009 | Lavelle | 623/23.66 |
| 7,731,676 B2 | 6/2010 | Maeda | 604/8 |
| 7,789,915 B2 | 9/2010 | Lavelle et al. | 623/23.66 |
| 7,914,809 B2 | 3/2011 | Atanasoska et al. | 424/423 |
| 7,946,999 B2 | 5/2011 | Rooney et al. | 600/585 |
| 2002/0040204 A1 * | 4/2002 | Dev et al. | 604/20 |
| 2002/0138129 A1 | 9/2002 | Armstrong et al. | 623/1.11 |
| 2004/0078088 A1 | 4/2004 | Gellman | 623/23.66 |
| 2004/0087886 A1 | 5/2004 | Gellman | 604/8 |
| 2005/0240278 A1 | 10/2005 | Aliski et al. | 623/23.7 |
| 2006/0095050 A1 | 5/2006 | Hartley et al. | 606/108 |
| 2006/0135981 A1 | 6/2006 | Lenker et al. | 606/191 |
| 2007/0005024 A1 | 1/2007 | Weber et al. | 604/265 |
| 2007/0021840 A1 | 1/2007 | Lopera | |
| 2007/0161967 A1 | 7/2007 | Fischer, Jr. et al. | 604/508 |
| 2007/0250149 A1 | 10/2007 | Von Oepen et al. | 623/1.11 |
| 2007/0276466 A1 * | 11/2007 | Lavelle et al. | 623/1.22 |
| 2009/0105719 A1 | 4/2009 | Honey et al. | 606/108 |
| 2009/0326647 A1 | 12/2009 | Quillin | 623/1.49 |
| 2010/0057189 A1 | 3/2010 | Kangas | 623/1.15 |
| 2010/0233021 A1 | 9/2010 | Sliwa et al. | 422/20 |
| 2010/0233263 A1 * | 9/2010 | Ludwig et al. | 424/484 |

FOREIGN PATENT DOCUMENTS

| | | | |
|---|---|---|---|
| WO | WO 00/74577 A1 | 12/2000 | A61B 17/12 |
| WO | WO 2010/063998 A2 | 10/2010 | A61K 47/48 |

OTHER PUBLICATIONS

Tenke, P., et al., Bacterial biofilm formation on urologic devices and heparin coating as preventive strategy, International Journal of Antimicrobial Agents 23S1 (2004) pp. S67-S74.

Extended European Search Report, European Patent Application No. 12183238.0 for "Electrically Charged Medical Device", Dated Nov. 21, 2012.

Official Communication Pursuant to Article 94(3) EPC for EP Application No. 12 183 238.0, dated Mar. 18, 2015, 5pp.

* cited by examiner

ELECTRICALLY CHARGED MEDICAL DEVICE

CROSS-REFERENCE TO RELATED APPLICATIONS

This application claims priority from U.S. Provisional Application No. 61/531,178 filed on Sep. 6, 2011, the entirety of which is hereby fully incorporated by reference herein.

SPONSORED RESEARCH OR DEVELOPMENT

The work leading to this invention has received funding from the European Community's Seventh Framework Programme (FP7/2007-2013) under grant agreement number 212533.

TECHNICAL FIELD

This disclosure relates to medical devices that may be placed within the body for a long term medical purpose. For example, the disclosure relates to stents that are configured for long term placement in a patient's urinary system to provide patency therethrough in clinical situations where the patency through the urinary system is compromised or blocked. It is a known problem with long indwelling devices within a patient, especially in the urinary tract that encrustation such as gradually growing magnesium and calcium deposits, develops and becomes deposited upon the device. The gradual growth of deposits upon the device normally thickens the walls of the device and gradually fouls or narrows the flow path within or around the device, often necessitating periodic removal and replacement of the device with a fresh device to maintain patency.

Some conventional indwelling devices, such as indwelling plastic ureteral stents attempt to minimize this problem with coatings of chemical and/or pharmacological agents, such as heparin, which have been observed to minimize or slow the growth of crystalline structures upon the deployed devices.

BRIEF SUMMARY

A first representative embodiment of the disclosure is provided. The embodiment includes a medical device with an elongate member extending between a distal end and a proximal end, with a lumen defined through at least a central portion of the member. The member is defined from a wire that is coiled to define the lumen therethrough, and the coils of the wire are configured such that a plurality of the neighboring coils define a small space therebetween. The coiled wire comprises a central metallic core that extends along the entire length of the wire defining the member and a polymeric jacket wrapped around the core, wherein the polymeric jacket is configured to retain an electric charge disposed therethrough.

Another representative embodiment of the disclosure is provided. The embodiment includes a method of manufacturing a stent. The method requires the step of coiling an elongate wire in a helical manner to define a proximal end portion, a distal end portion, and a lumen extending at least partially therethrough. The wire comprises a metallic core that extends along the entire length of the wire and a polymeric jacket wrapped around the core. The method further includes the step of charging the polymeric jacket such that the polymeric jacket retains an electric charge.

Advantages of the disclosed device will become more apparent to those skilled in the art from the following description of embodiments that have been shown and described by way of illustration. As will be realized, other and different embodiments are contemplated, and the disclosed details are capable of modification in various respects. Accordingly, the drawings and description are to be regarded as illustrative in nature and not as restrictive.

DETAILED DESCRIPTION OF THE DRAWINGS AND THE PRESENTLY PREFERRED EMBODIMENTS

Recent experimentation and empirical analysis of the mechanisms of growth of crystalline structures upon indwelling devices, such as ureteral stents, has shown that devices that have been coated with a chemical or pharmacological compound, such as Heparin, have exhibited minimized or slowed growth of crystalline structures thereupon or other surface fowling of indwelling ureteral stents. It has been determined that the reduction or slowing of crystalline growth is not directly due to a chemical or pharmacological reaction between the treated surface and the liquid flowing past the exposed surfaces of the indwelling devices, but due to an electrically negative potential created upon the coated exposed surfaces, which is thought to repel the cellular organisms from the surface of the device, which are the precursor of the formation of the various deposits upon the surfaces of the device. Recent research has been ongoing to develop alternatives to chemical and pharmacological coatings upon indwelling devices, and to other methods of forming devices that exhibit the same electrically negative potential at their surface to similarly minimize surface fowling or formation of deposits thereupon.

Figure 1:
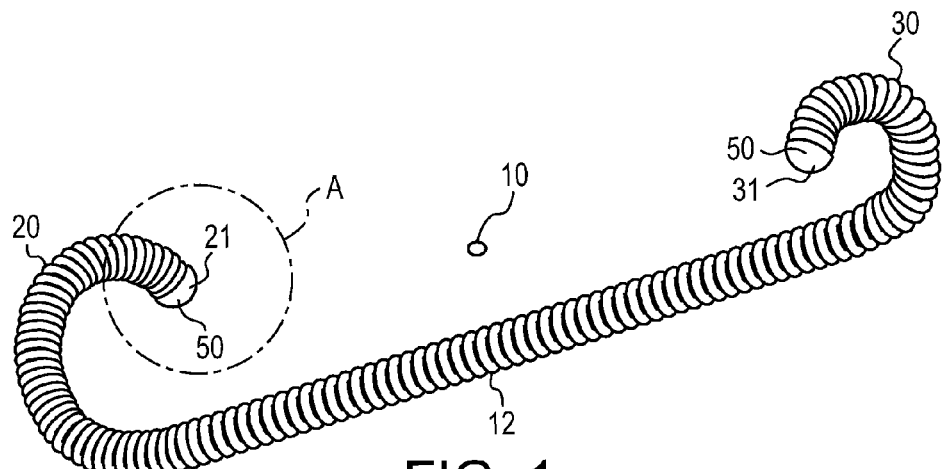
FIG. 1 is a perspective view of a coiled medical device.
Figure 2:
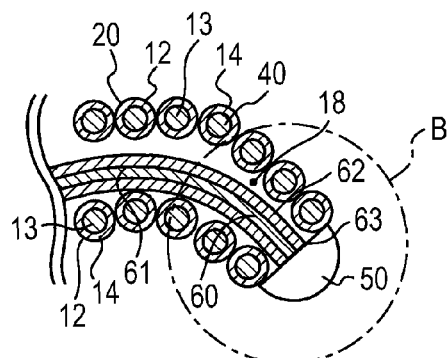
FIG. 2 is a cross-sectional detail view of detail A of FIG. 1.
Figure 3:
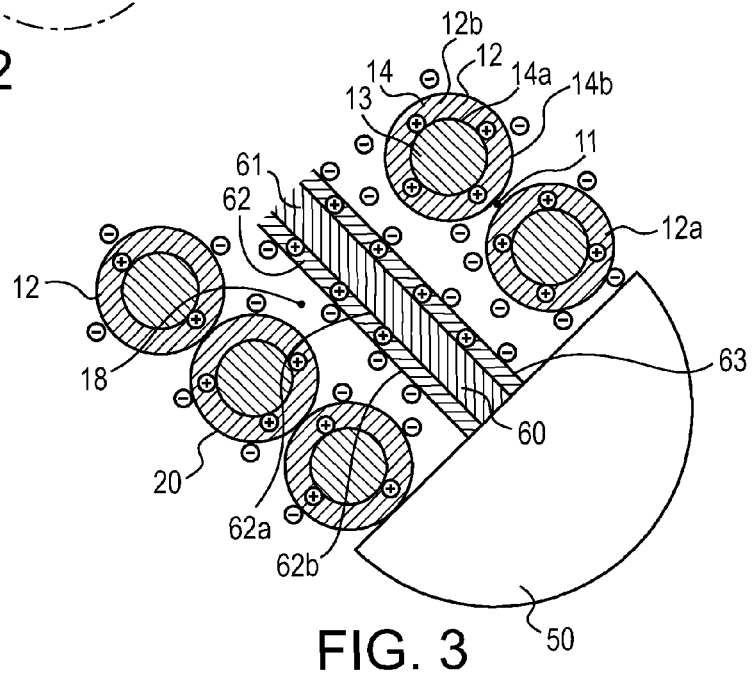
FIG. 3 is a cross-sectional detail view of detail B of FIG. 2.

Turning now to FIGS. 1-3, a medical device 10 is provided. The medical device 10 includes a wire that is tightly coiled to form a plurality of coils 12 that define a lumen 18 therethrough and extend between a distal end portion 20 and a proximal end portion 30. The coiled wire 12 may be configured such that the device 10 is substantially flexible such that neighboring coils (12a, 12b, FIG. 3) either contact each other, or are in close proximity to each other to define a small space 11 therebetween, depending on the orientation of that portion of the device 10. The device 10 is configured such that fluid, such as urine, can extend from outside of the device 10 and into the lumen 18 through one or more of the spaces 11 established between neighboring coils (FIG. 3, schematically), flow through a portion or the entirety of the lumen 18 and then leave the device 10 through one or more of the spaces 11 between neighboring coils at a different portion of the device 10.

In some embodiments, the device 10 may further include a safety wire 60 that extends between the distal end portion 20 and the proximal end portion 30 of the device 10. The safety wire 60 may be fixed to one or both of the distal and proximal end tips 21, 31 that form the outermost portion of the respective distal and proximal end portions 20, 30. Alternatively, the safety wire 60 may be fixed to one or both of the distal and proximal end portions 20, 30 inboard of the tips 21, 31. The entire safety wire 60 may extend through the lumen 18, while in other embodiments, all or a portion of the safety wire 60 may extend outside of the lumen 18. In some embodiments, a portion of the safety wire 60 may extend through the lumen 18 and another portion of the safety wire 60 may extend outside of the lumen 18, with the safety wire 60 transitioning therebetween through a space 11 between neighboring coils. As can be understood with reference to the subject specification and drawings, the safety wire 60 is configured to establish a constant length of the device 10 (or at least a constant length of the portion through which the safety wire 60 extends), while allowing the device 10 to be sufficiently flexible to travel through a tortuous path within the anatomy of a patient. The safety wire 60 further is provided to prevent the elastic elongation of the coiled wire 12, especially during implantation and removal.

One or both the wire defining the coil 12 and the safety wire 60 may be formed from an inner core and an outer coating of differing materials. Specifically, the coil 12 may be formed from a continuous inner core 13, which may be metallic and may either be of a monolithic or a multi-fiber construction, and a continuous polymeric jacket, or outer coating 14, which may be a polymer or another type of material. Similarly, the safety wire 60 may be formed from an inner core 61, which may be metallic, which may be of a monolithic or a multi-fiber construction, and a continuous polymeric jacket, or outer coating 62, which may be a polymer or another type of material.

The coil 12 may be defined from an inner core 13 and an outer coating 14. The inner core 13 may be a monolithic or monofilament electrically conductive member that extends along the entire length of the coil 12. In some embodiments, the inner core 13 may be metallic. In some embodiments, the inner core 13 may be an alloy of several metallic members, such that the overall inner core 13 is electrically conductive. In other embodiments, the inner core 13 may be made from several components that in total extend the length of the coil 12 in an end to end relationship, which are each electrically connected together such that an electric current passed into one end of the inner core 13 reaches an opposite end of the inner core 13 with minimal electrical resistance losses therealong due at the one or more connection points.

In some embodiments, the inner core 13 may be formed from a nickel-cobalt alloy, or a cobalt-chrome alloy, (such as MP35N, Elgiloy, or L605), Nickel Titanium alloys (such as Nitinol) or other materials, such as a various stainless steel alloys (such as 316L or 316SS), or MP159, Astroloy M, Inconnel 625, 35NLT, Biodur 108 and Hastelloy S. Moreover, composite alloys of the above mentioned alloys with a central core of a different material (such as gold, platinum, tantalum, silver, tungsten, and the like may be used for the inner core 13. Other suitable characteristics for materials that could be selected to form the inner core 13 are materials that have sufficient hoop strength when coiled to maintain the patency of the lumen 18 defined by the coiled wire 12 and resist kinking, in the presence of typical strictures or narrowing formations within the ureter, as well as the typical inward force disposed upon the device 10 by the patient's anatomy as the device 10 traverses the tortuous path through the patient's urinary system. For example, for devices 10 that are configured to be ureteral stents, the typical coiled wire 12 outer diameter may be 1.67 mm (5 Fr), 2.0 mm (6 Fr), 2.33 mm (7 Fr), or 2.67 mm (8 Fr). including the diameter of the outer coating 14. Typical lengths of ureteral stents are between 12 and 30 cm, inclusive of various and all lengths therein. As a related matter, the material chosen for the inner core 13 must be sufficiently flexible (with the required hoop strength, as discussed above) to easily navigate the tortuous path through the patient, and be able to be formed in (and remember) a tightly wound configuration, such as by training the device 10 to form "pigtails" on one or both end portions 20, 30 of the device 10, with the pigtailed portions being flexible enough to be substantially elongated into a relatively straight configuration while introducing the device 10 into the patient.

The outer coating 14 may extend around the entire circumference of the inner core 13 along the entire length of the inner core 13. In other embodiments, the outer coating 14 may extend around substantially the entire circumference of the inner core 13, and may expose a small portion of the inner core 13 through a seam or other aperture. The outer coating 14 may be a polymer, such as a fluoropolymer that is configured to provide the coil 12 with a low friction surface to allow the device 10 to be easily inserted into the position within the patient, especially through the tortuous path found through a male patient's urethra and ureter in embodiments where the device 10 is a ureteral stent. The outer coating 14 may additionally be formed from a material that is capable of obtaining and retaining an electric charge therewithin, even in moist and humid environments, such as a patient's ureter (with opposite end portions 20, 30 disposed within the patient's kidney and bladder, respectively).

The outer coating 14 may be one that will retain a positive electric charge upon an inner surface 14a thereof (as shown schematically in FIG. 3 with a plurality of "+" symbols), i.e. the portion of the outer coating 14 that contacts an outer surface of the inner core 13, with the outer surface 14b of the outer coating 14 retaining a negative electric charge (as shown schematically in FIG. 3 with a plurality of "−" symbols). The material chosen to form the outer coating 14 should act as a sufficient dielectric to minimize the electrical communication through the material between the oppositely charged surfaces thereof with the suitable outer coating thickness to minimize the overall diameter of the device 10 for a given inner diameter of the lumen 18. The typical suitable thickness of the outer coating may be between about 5 and 25 microns, inclusive of all thicknesses therewithin. In some embodiments, the outer coating 14 may be formed from Polyvinylidene Fluoride (PVDF). In other embodiments, the outer coating may be a polymeric material that is substantially PVDF. Alternatively, the outer coating 14 may be a co-polymer of PVDF and another polymeric material, such as PTFE, PVDF-trifluoroethylene (TrFE), and the like.

The safety wire 60 may be made similarly to the coil 12. In some embodiments, the safety wire 60 may include an inner core 61 and an outer coating or polymeric jacket 62. The inner core 61 may be a monolithic or monofilament of an electrically conductive material that extends along the entire length of the safety wire 60. In other embodiments, the inner core 61 may be formed from a plurality of several components that in total extend the length of the safety wire 60 in an end to end relationship, which are each electrically connected together such that an electric current passed into one end of the inner core 61 reaches an opposite end of the inner core 61 with minimal electrical resistance losses therealong due at the one or more connection points. In some embodiments, the inner core 61 may be metallic. In some embodiments, the inner core 61 may be an alloy of several metallic members, such that the inner core 61 is electrically conductive along its length. Like the inner core 13 of the coil 12, the inner core 61 of the safety wire 60 may be formed from nickel-cobalt alloy, or a cobalt-chrome alloy, (such as MP35N, Elgiloy, or L605), Nickel Titanium alloys (such as Nitinol) or other materials, such as various stainless steel alloys (such as 316L or 316SS), or MP159, Astroloy M, Inconnel 625, 35NLT, Biodur 108 and Hastelloy S. Moreover, composite alloys of the above mentioned alloys with a central core of a different material (such as gold, platinum, tantalum, silver, tungsten, and the like) may be used for the inner core 13. In some embodiments, the safety wire 60 may be formed from other materials or alloys that are electrically conductive yet rigid enough to minimize stretching, which maintains the coiled portion of the device that the safety wire 60 is connected thereto at a constant length, with the normal bending of the device 10 (both the trained configuration of the device 10 as well as when passing the device 10 through the tortuous path when the device 10 is deployed).

In some embodiments, the safety wire 60 may additionally include an outer coating 62 that is formed similarly to, or like the outer coating 14 of the coiled wire 12. When provided, the outer coating 62 is configured to obtain and store an electrically negative charge at an outer surface 62b thereof, and obtain and store an electrically positive charge at an inner surface 62a thereof, i.e. at the surface that contacts the inner core 61 of the safety wire 60 (FIG. 3). As will be discussed in further detail below, the outer coating 62 of the safety wire 60 may obtain the electrically negative charge upon its outer surface independently of the charging of the coiled wire 12, or in other embodiments discussed below, the outer coating 62 of the safety wire 60 may obtain an electrically negative charge at its outer surface 62b at the same time as the coiled wire 12 is charged.

Figure 4:
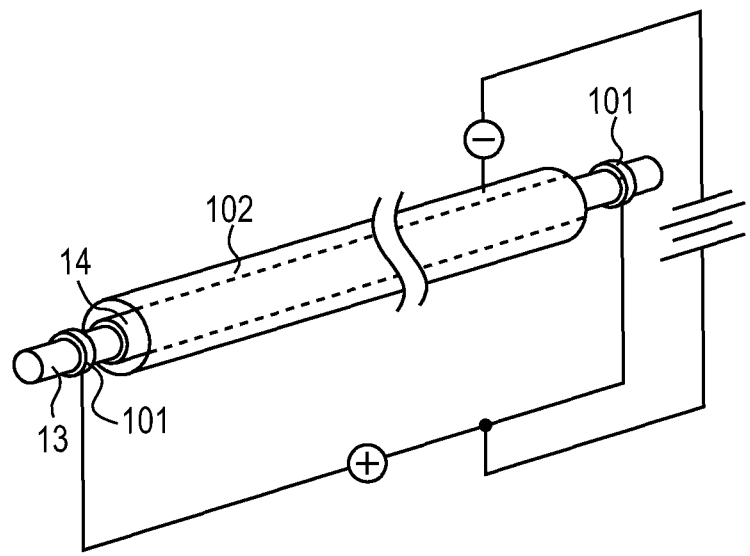
FIG. 4 is a schematic view of a first structure to charge the wire that becomes the coiled wire within the medical device of FIG. 1, prior to coiling.

Turning now to FIGS. 4-8, several methods of electrically negatively charging the outer surface 14b of the outer coating 14 are discussed and depicted schematically. Turning first to FIG. 4, the outer surface 14b of the outer coating 14 may be negatively charged by contact polling the wire before the combined core 13 and outer coating 14 (the wire) is coiled to form the coiled wire 12. Specifically, one or both of the opposite ends of the inner core 13 are electrically connected to a positive electrode 101, with the outer coating 14 removed at the contact point between the positive electrode 101 and each end of the core 13. The positive electrode 101 may be a wire clamp, alligator clip, or other conventional electrical connection device. Simultaneously, a tubular electrode 102, or an electrode jacket 102a (FIG. 4a), which contacts a majority of the circumference of the outer coating 14 and may be opened and closed about the outer coating 14, is positioned around and in contact with the outer coating 14 of the wire. The tubular electrode 102 (or electrode jacket 102a) is at a negative electrical potential with the entire length, or a portion of the length, of the wire disposed within and in contact with the tubular electrode 102 (or electrode jacket 102a). In some embodiments, the tubular electrode 102 may be a foil or other metallic wrapping around the outer coating 14 which makes contact with the outer coating 14 about a significant portion of the outer surface 14b thereof.

Figure 4A:
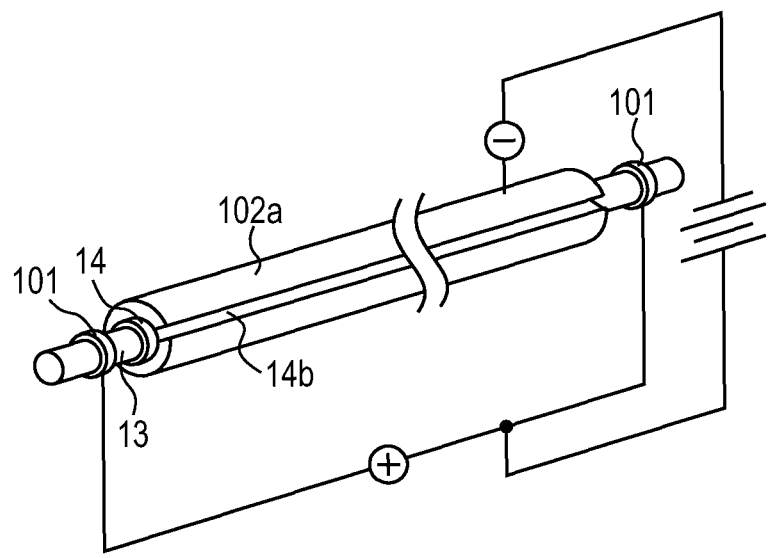
FIG. 4a is a schematic view of a second structure to charge the wire that becomes the coiled wire within the medical device of FIG. 1, prior to coiling.
Figure 4B:
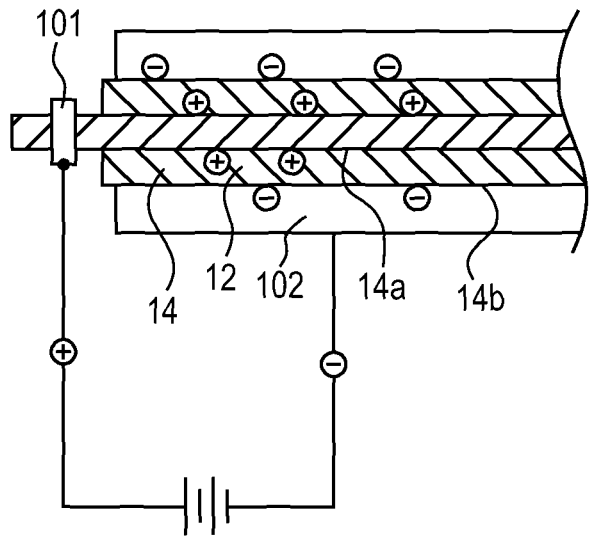
FIG. 4b is a cross-sectional view of a portion of the first structure of FIG. 4.
Figure 5:
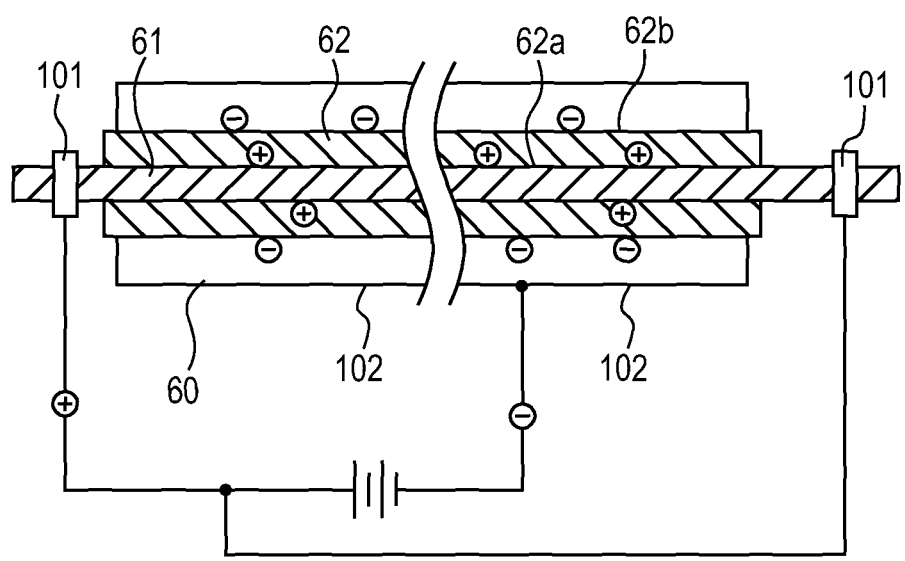
FIG. 5 is a cross-sectional schematic view of a structure to charge a safety wire used in the coiled medical device of FIG. 1.

As shown schematically in the detail view side view presented in FIG. 4b, and with further reference to FIGS. 4 and 4a, when both of the positive and negative electrodes are simultaneously energized, the inner surface 14a of the outer coating 14 along the length of the wire adopts a positive electrical potential about substantially the entire circumference thereof, (depicted schematically with multiple "+" symbols), and the outer surface 14b of the length of the wire within the tubular electrode 102 (electrode jacket 102a) obtains a negative electrical charge about substantially the entire circumference thereof (depicted schematically with multiple "−" symbols), or at least the portions of the outer surface 14b of the outer coating 14 that contact the tubular electrode 102. In embodiments where the tubular electrode 102 (electrode jacket 102a) is less than the length of the wire that forms the coiled section 12, the wire is then moved with respect to the tubular electrode 102 (electrode jacket 102a) to negatively charge another portion of the wire, and again moved (if needed) with respect to the tubular electrode 102 (electrode jacket 102a) to charge yet another portion of the wire until the entire wire is charged.

Subsequent to the positive charging of the inner surface 14a of the outer coating 14 and negatively charging the outer surface 14b of the outer coating 14, the wire is mechanically coiled using a conventional coiling machine. In some embodiments, one or both of the uncovered ends of the inner core 13 may be clipped such that the entire coiled wire 12 is covered with an outer coating 14 along its length. As shown in FIGS. 2 and 3, in embodiments with a safety wire 60, the safety wire 60 may be threaded through the lumen 18 (or otherwise disposed with respect to the coiled wire 12 as discussed above) of the coiled wire 12 with a first end 63 of the safety wire 60 fixed to a distal end portion 20 of the coiled wire 12 and an opposite end (not shown, but representative of the first end 63) of the safety wire 60 fixed to a proximal end portion 30 of the coiled wire 12. In some embodiments, where one or both of the distal and proximal end portions 20, 30 of the coiled wire 12 receives a weld bead 50 or the like to fully or partially close the lumen 18 at each end, the weld bead 50 receives and fixes one end 63 of the safety wire 60 with the distal end portion 20 of the coiled wire 12 and/or the opposite end of the safety wire 60 with the weld bead 50 and the proximal end portion 30 of the coiled wire 12.

In some embodiments where the safety wire 60 includes both an inner core 61 and an outer coating 62 that is capable of retaining an electric charge, the outer coating 62 of the safety wire 60 may be negatively charged using contact polling, similar to the method discussed above for charging the outer coating 62 of the wire that becomes the coil 12. As depicted schematically in FIG. 5, one or both of the opposite ends of the inner core 61 are electrically connected with a positive electrode 101 to pass a positive charge therethrough, while the safety wire 60 (either the entire length of the safety wire 60, or a portion of the length of the safety wire 60) is passed therethrough to make surface contact with a tubular electrode 102 (electrode jacket 102a) that is at a negative charge. When both the positive and negative electrodes are energized, the inner surface 62a of the outer coating 62 becomes positively charged along its length (and about substantially the entire circumference thereof) and the outer surface 62b of the outer coating 62 becomes negatively charged (about substantially the entire circumference thereof, or at least upon the portions of the outer surface 62b of the outer coating 62 that contact the tubular electrode 102 (electrode jacket 102a)). The charged safety wire 60 is fixed to the coiled wire 12, to prevent elongation of the coiled wire 12 as the device 10 is deployed within the patient.

Figure 6:
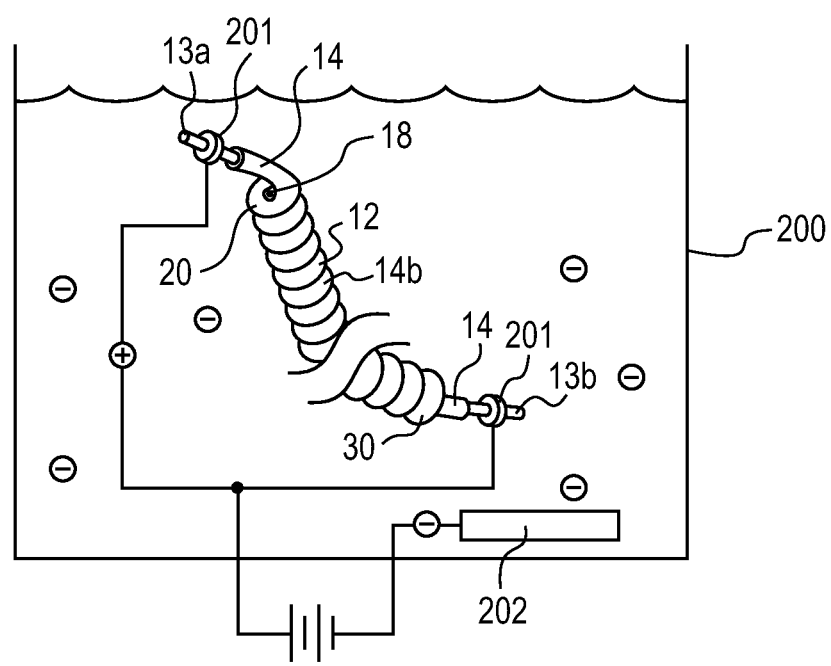
FIG. 6 is a schematic view of a charging bath used to charge a coiled wire to that becomes the medical device of FIG. 1.

In an alternate method of forming the device 10, the inner core 13 may be suitably coated with a fluoropolymer capable of receiving and retaining an electric charge, such as PVDF or other suitable materials discussed above, and the coiled wire 12 is then formed with a suitable diameter, length, and pitch to form the desired dimensions of the device, using conventional coiling methods known by those of ordinary skill in the art. As shown in FIG. 6, after formation of the plurality of coils, the outer coating 14 is removed from one or both of the opposite end tips 13a, 13b of the coiled wire 12 and one or both of the end tips are connected to a positive electrode 201. The coiled wire 12 is then disposed within a negatively charged environment. For example, the coiled wire 12 may be disposed within a bath 200 filled with a liquid that is capable of passing an electric charge therethrough, such as ionized water, or other liquids that can efficiently pass current therethrough. The liquid bath 200 receives a negative electrode 202, or the liquid within the bath 200 is in electrical communication with the negative electrode 202. The source of positive and negative electrical charge to the positive and negative electrodes (shown schematically as a battery in FIG. 6, as well as FIGS. 6a-7a of other embodiments discussed below) is depicted as existing outside of the bath, with conductors transferring the charge to the electrodes. One of ordinary skill in the art will understand with reference to the subject application that these conductors may be insulated within the bath to avoid short circuiting the positive and negative charges in the presence of the conductive liquid or gas.

Figure 6A:
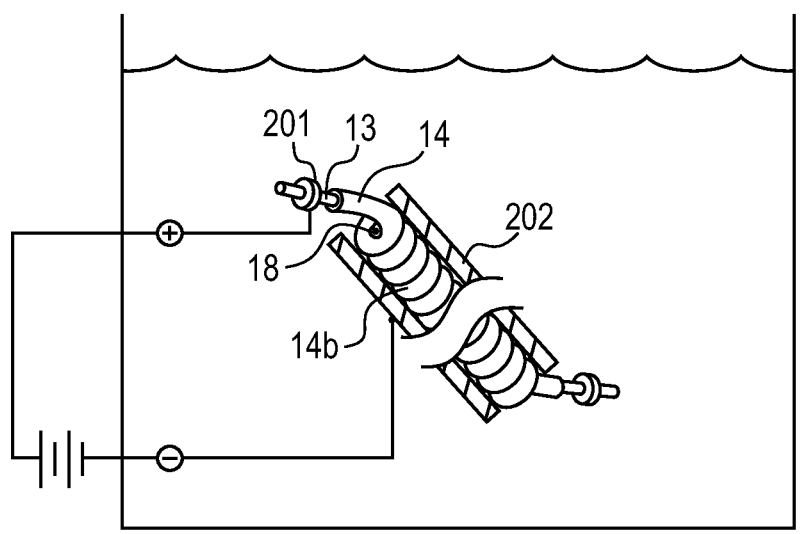
FIG. 6a is a schematic view of the charging bath of FIG. 6, wherein the negative electrode is a tubular electrode that surrounds the coiled wire.

In some embodiments shown in FIG. 6a, the negative electrode 202 may be a tubular structure that receives the coiled wire 12 within its lumen to establish surface contact between an outer surface 14b of the outer coating 14. When the negative electrode 202 and the coiled wire 12 are submerged within the conducting liquid (or gas as discussed below) bath, the conductive medium eliminates any air gap between the negative electrode and the surfaces of the coiled wire 12, including the surfaces of the coiled wire 18 within the lumen 18, which conducts the negative electrical potential through the spaces 11 defined between neighboring coils 12a, 12b (FIG. 3). In some embodiments, the conductive bath (air or gas) may be placed in a vacuum to further eliminate any air bubbles or otherwise solubilized air or other gas within the conductive bath, to further increase the conductance within the bath.

The positive and negative electrodes 201, 202 are both energized, which causes the inner surface 14a of the outer coating 14 to develop a positive electrical charge, and the outer surface 14b of the outer coating 14 to develop a negative charge (as depicted schematically in FIG. 3, showing the fully assembled device 10, i.e. with a safety wire 60 attached thereto). As can be understood, as with the other embodiments where the outer surface 14b of the outer coating 14 is negatively charged, substantially the entire periphery of the outer coating 14 includes the negative charge, including the portions disposed within the lumen 18 and the portions that are proximate to or touch the coating of neighboring coils depending on the orientation of the device 10. In further embodiments, the coiled wire 12 can be placed in a bath (or an enclosed environment) filled with a highly conductive gas with a negative electrode disposed therein to fully charge the outer surfaces of the coiled wire 12.

After the outer coating 14 is sufficiently charged, a safety wire 60 (either an uncoated wire, or a coated wire, with an outer coating 62 that may be negatively charged, as described above) is passed through the lumen 18 of the device 10 (or otherwise disposed with respect to the coiled wire 12 as discussed above) and fixed to the opposite distal and proximal end portions 20, 30 of the coiled wire 12. One or both of the distal and proximal end portions 20, 30 may then be fully or partially closed with weld beads 50 (or the like) applied thereto, which may also fix each end of the safety wire 60 to the respective end of the coiled wire 12.

Figure 7:
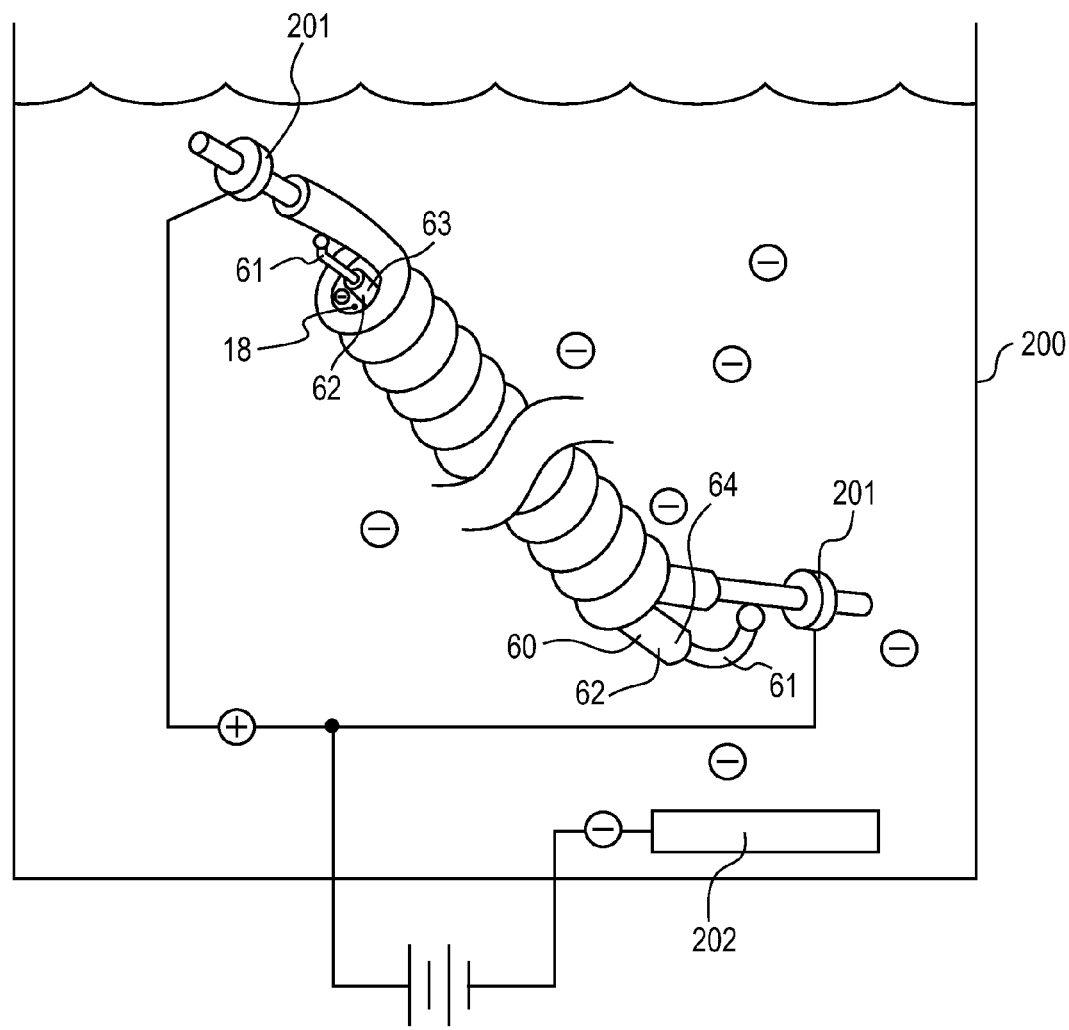
FIG. 7 is a schematic view of another charging bath to charge both a coiled wire and safety wire that become the medical device of FIG. 1.

As depicted in FIG. 7, the coiled wire 12 and the safety wire (when formed with the polymeric jacket or outer coating 62) may be assembled and then simultaneously charged. For example, the coiled wire 12 may be formed into the desired diameter, length, and wire pitch for use in the final indwelling device 10, such as a ureteral stent and the safety wire 60 may then be threaded through a lumen 18 of the coiled wire 12 (or otherwise disposed with respect to the coiled wire 12 as discussed above). The outer coating 14 of the coiled wire 12 is removed at the proximal and distal end tips thereof, and the outer coating 62 at the opposite end tips of the safety wire 60 is similarly removed. The tip of the distal end portion 20 is then fixed to the neighboring tip of the safety wire 60 to establish metal-to-metal contact therebetween (or at least placed into electrical contact), and the tip of the proximal end portion 30 and the exposed tip of the opposite end of the safety wire 60 are similarly connected with metal-to-metal contact (or at least placed into electrical contact). One or more positive electrodes 101, similar to those discussed above, are attached to one or both of the opposite connected end tips of the coiled wire 12 and the safety wire 60, such that the combined coiled wire 12 and the safety wire 60 are wired in parallel between the positive electrodes. The entire device 10 may then be dipped within a bath (as discussed above) that includes a negative electrode 202, or similar to the embodiment depicted in FIG. 6a and discussed above, the negative electrode 202 may be a tube through which the device 10 is passed through the lumen thereof. As with the embodiments discussed above, energizing both positive and negative electrodes results in a positive charge upon the inner surface (14a, 62a) of the outer coatings 14, 62 and a negative charge upon the outer exposed surface (14b, 62b) of the outer coatings 14, 62 (as depicted schematically in FIG. 3).

Figure 7A:
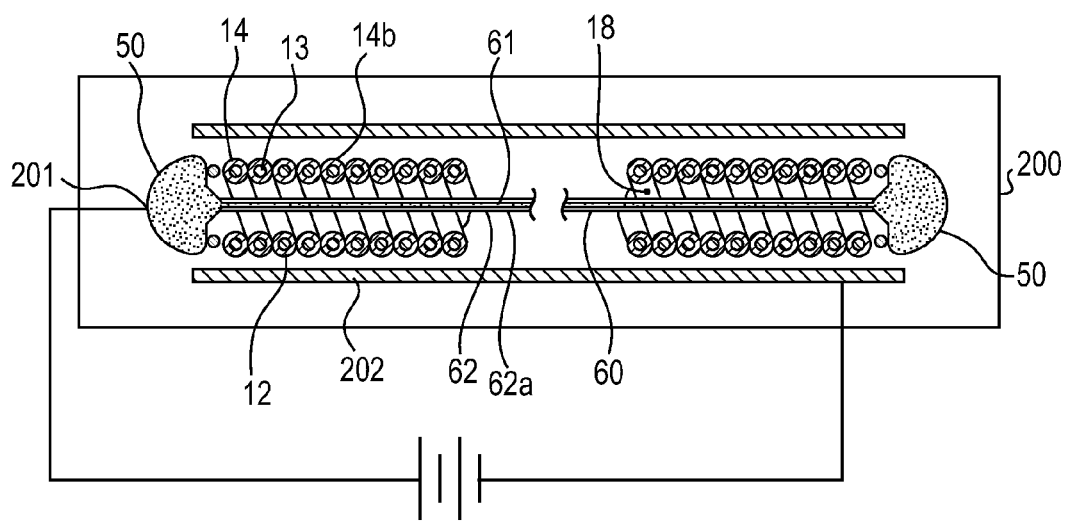
FIG. 7a is a schematic view of yet another charging bath to charge both a coiled wire and safety wire that become the medical device of FIG. 1.

Alternatively, as shown in FIG. 7a, the fully assembled device 10, including the weld beads 50 on opposite ends of the device 10 may be charged. The outer coating 14 of the coiled wire 12 is removed just proximate to each weld bead 50 to confirm electrical contact between the weld bead 50 and the inner core 13. Similarly, the inner core 61 of the safety wire 60 is received within one or both of the weld beads 50, to establish electrical contact therebetween. A positive electrode 201 may be fixed to one or both of the weld beads 50 (which provides a positive charge both the inner core 13 of the coiled wire 12 and the inner core 61 of the safety wire 60 when energized). A negative electrode 202, such as a tubular electrode as depicted in FIGS. 7a and 6a, is placed around the coiled wire 12 to contact or be in close proximity to the outer coating 14 of the coiled wire 12. The device is placed within the liquid or gas bath, similar to the baths discussed in the embodiments above. Upon energizing the positive and negative electrodes 201, 202, the outer surface 14b of the coiled wire 12 (both outside and inside the lumen 18) and the outer surface 62a of the safety wire 60 each reach a negative electrical potential, as discussed above and shown schematically in FIG. 3.

Figure 8:
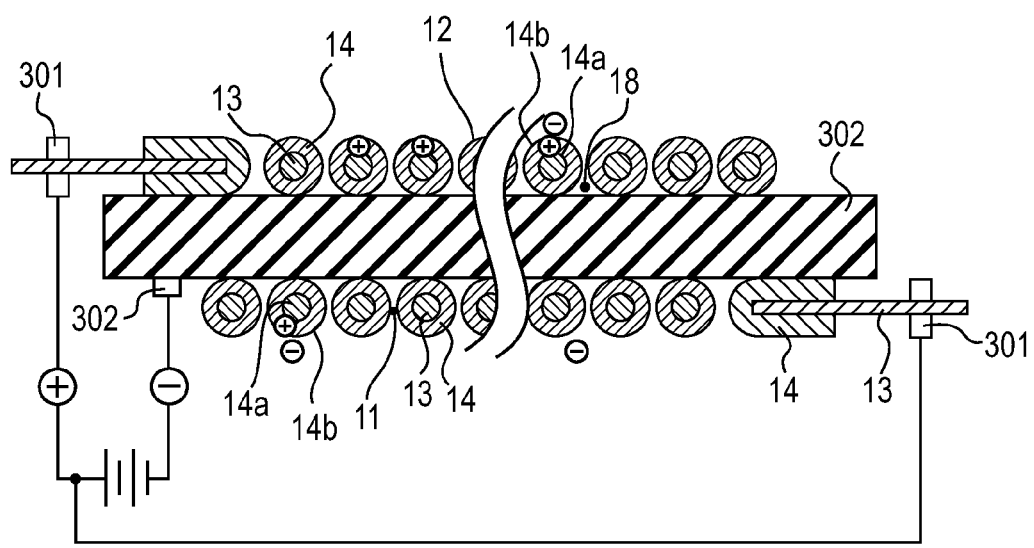
FIG. 8 is a schematic cross-sectional view of another structure to charge a coiled wire that becomes the medical device of FIG. 1, after coiling.

In yet another method of forming the device 10 depicted in FIG. 8, the inner core 13 may be suitably coated with a fluoropolymer capable of receiving and retaining an electric charge, such as PVDF, and the coiled wire 12 is then formed with a suitable diameter, length, and pitch to form the desired dimensions of the device, using conventional coiling methods known by those of ordinary skill in the art. As shown in FIG. 8, after formation of the plurality of coils 12, the outer coating 14 is removed from the opposite end tips of the coiled wire 12 and one or both of the end tips are connected to a positive electrode 201. A thin negative electrode 302 is then passed through the lumen 18 of the coiled wire 12 such that the electrode 301 contacts the outer coating 14 disposed within the lumen 18 of all or a significant number of coils of the coiled wire 12 of the device 10. The two opposite electrodes are then energized to cause the inner surface 14a of the outer coating 14 to be a positive charge and the outer surface 14b of the outer coating 14 to be at a negative charge. In some embodiments, the negative electrode 302 may be connected in series with a tubular electrode (similar to the tubular electrodes 202, discussed above and depicted in FIGS. 6a and 7a) to increase the overall charged members contacting or located in close proximity to the outer surface 14b of the coiled wire 12 and the outer surface 62a of the safety wire, to increase the effectiveness of negatively charging of the outer surfaces 14b, 62b of the coiled wire 12 and the safety wire 60.

While the preferred embodiments of the disclosure have been described, it should be understood that the disclosure is not so limited and modifications may be made without departing from the invention. The scope of the invention is defined by the appended claims, and all devices that come within the meaning of the claims, either literally or by equivalence, are intended to be embraced therein.

The invention claimed is:

1. A medical device comprising:
an elongate member extending between a distal end and a proximal end, with a lumen defined through at least a central portion of the member, the member is defined from a wire that is coiled to define the lumen therethrough, the coils of the wire are configured such that a plurality of the neighboring coils define a small space therebetween,
the coiled wire comprises a central metallic core that extends along the entire length of the wire defining the member and a polymeric jacket wrapped around the core, wherein the polymeric jacket is configured to retain an electric charge disposed therethrough,
wherein the polymeric jacket includes a negative electric charge at an outer surface thereof, and a positive electric charge at an inner surface thereof, which contacts or is in close proximity to the metallic core, wherein the polymeric jacket does not include a pharmacological coating.

2. The device of claim 1, wherein the lumen extends through a central portion of the device and the distal and proximal end tips that are disposed upon the respective distal and proximal end portions are closed to prevent access to the lumen therethrough.

3. The device of claim 1, further comprising a second wire disposed within the lumen, a first end of the wire fixed to the distal end portion, a second end of the wire fixed to the proximate end portion, wherein the wire prevents elongation and contraction of the elongate member.

4. The device of claim 3, wherein the second wire comprises a metallic core and the polymeric jacket wrapped therearound.

5. The device of claim 4, wherein the core of the second wire is fixed to the core of the coiled wire.

6. The device of claim 1, wherein the proximal and distal end portions are each biased to a pigtail configuration, but are sufficiently flexible to be urged into a straight configuration.

7. The device of claim 1, wherein the polymeric jacket comprises a ferroelectric polymer.

8. The device of claim 7, wherein the polymeric jacket is PVDF.

9. The device of claim 1, wherein the polymeric jacket is a copolymer of PVDF.

10. The device of claim 1, wherein the metallic core uniformly extends along the entire length of the wire.

* * * * *